(12) United States Patent
Willis et al.

(10) Patent No.: US 6,908,449 B2
(45) Date of Patent: Jun. 21, 2005

(54) SEALING VALVE ASSEMBLY FOR MEDICAL PRODUCTS

(75) Inventors: Allan F. Willis, Evesham, NJ (US); Alan Conlin, Pocatello, ID (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/741,730

(22) Filed: Dec. 19, 2000

(65) Prior Publication Data

US 2002/0077604 A1 Jun. 20, 2002

(51) Int. Cl.$^7$ ............... A61M 29/00; A61M 37/00; A61M 31/00; A61F 11/00
(52) U.S. Cl. ............... 604/96.01; 604/103.06; 604/103.07; 604/514; 606/108
(58) Field of Search ............ 604/103.06, 256, 604/103.07, 247, 514, 167.03, 916, 96.01, 167.04, 93.01, 533, 500, 174, 27; 606/108, 193; 600/30, 3

(56) References Cited

U.S. PATENT DOCUMENTS

| | | |
|---|---|---|
| 4,390,017 A | 6/1983 | Harrison et al. |
| 4,511,163 A | 4/1985 | Harris et al. |
| 4,594,074 A | 6/1986 | Andersen et al. |
| 4,666,433 A | 5/1987 | Parks |
| 4,685,901 A | 8/1987 | Parks |
| 4,717,385 A | 1/1988 | Cameron et al. |
| 4,798,592 A | 1/1989 | Parks |
| 4,798,594 A * | 1/1989 | Hillstead ............ 604/167.04 |
| 4,799,923 A | 1/1989 | Campbell |
| 4,834,712 A | 5/1989 | Quinn et al. |
| 4,850,953 A | 7/1989 | Haber et al. |
| 4,863,438 A | 9/1989 | Gauderer et al. |
| 4,944,732 A | 7/1990 | Russo |
| 4,959,055 A | 9/1990 | Hillyer |
| 4,960,412 A | 10/1990 | Fink |
| 5,057,093 A | 10/1991 | Clegg et al. |
| 5,080,650 A | 1/1992 | Hirsch et al. |
| 5,092,850 A | 3/1992 | Buma |
| 5,125,897 A | 6/1992 | Quinn et al. |
| 5,141,498 A | 8/1992 | Christian |
| 5,234,417 A | 8/1993 | Parks et al. |
| 5,250,040 A | 10/1993 | Parks et al. |
| 5,267,969 A | 12/1993 | Hirsch et al. |
| 5,267,983 A | 12/1993 | Oilschlager et al. |
| 5,273,529 A | 12/1993 | Idowu |
| 5,290,250 A | 3/1994 | Bommarito |
| 5,342,321 A | 8/1994 | Potter |
| 5,372,578 A | 12/1994 | Kriesel et al. |

(Continued)

FOREIGN PATENT DOCUMENTS

| | | |
|---|---|---|
| EP | 0140446 | 5/1985 |
| WO | 9906099 | 2/1999 |
| WO | 9945983 | 9/1999 |
| WO | 9952577 | 10/1999 |

OTHER PUBLICATIONS

U.S. Appl. No. 09/741,729, filed Dec. 19, 2000.
EPO Search Report, Jul. 15, 2002.

*Primary Examiner*—Nicholas D. Lucchesi
*Assistant Examiner*—Roz Maiorino
(74) *Attorney, Agent, or Firm*—Dority & Manning, P.A.

(57) ABSTRACT

A sealing valve assembly is provided for medical products. The valve assembly includes a valve member mountable within a passageway of a medical product body element, the valve member defining a peripheral portion spaced from a central axis and including two walls extending from the peripheral portion toward the central axis. The walls include ends that contact each other to preclude flow through the passageway. The valve member may be formed of a material having a durometer of less than about 20 Shore. The value member may also have a higher durometer material with other wall configurations, or may have a wall member having a varying durometer.

12 Claims, 3 Drawing Sheets

U.S. PATENT DOCUMENTS

| | | | |
|---|---|---|---|
| 5,399,173 | A | 3/1995 | Parks et al. |
| 5,403,290 | A | 4/1995 | Noble |
| 5,413,565 | A | 5/1995 | Michels et al. |
| 5,451,212 | A | 9/1995 | Andersen |
| 5,549,657 | A | 8/1996 | Stern et al. |
| 5,554,140 | A | 9/1996 | Michels et al. |
| 5,555,898 | A | 9/1996 | Suzuki et al. |
| 5,569,222 | A | 10/1996 | Haselhorst et al. |
| 5,681,294 | A | 10/1997 | Osborne et al. |
| 5,716,347 | A | 2/1998 | Gibbs et al. |
| 5,718,691 | A | 2/1998 | Russo |
| 5,720,734 | A * | 2/1998 | Copenhaver et al. ....... 604/247 |
| 5,735,841 | A | 4/1998 | Bourguignon et al. |
| 5,738,661 | A | 4/1998 | Larice |
| 5,772,255 | A | 6/1998 | Osborne et al. |
| 5,776,117 | A | 7/1998 | Haselhorst et al. |
| 5,820,614 | A | 10/1998 | Erskine et al. |
| 5,836,924 | A | 11/1998 | Kelliher et al. |
| 5,848,997 | A | 12/1998 | Erskine et al. |
| 5,865,816 | A | 2/1999 | Quinn |
| 5,895,377 | A | 4/1999 | Smith et al. |
| 5,988,700 | A | 11/1999 | Prichard |
| 5,997,503 | A | 12/1999 | Willis et al. |
| 6,015,400 | A | 1/2000 | Ross et al. |
| 6,019,746 | A | 2/2000 | Picha et al. |
| 6,030,361 | A | 2/2000 | Miyashiro |
| 6,045,536 | A | 4/2000 | Meier et al. |
| 6,050,934 | A * | 4/2000 | Mikhail et al. ...... 128/DIG. 25 |
| RE36,702 | E | 5/2000 | Green et al. |
| 6,066,112 | A | 5/2000 | Quinn |
| 6,264,631 | B1 * | 7/2001 | Willis et al. ........... 604/103.06 |
| 2001/0049501 | A1 * | 12/2001 | Osbourne et al. |

\* cited by examiner

US 6,908,449 B2

SEALING VALVE ASSEMBLY FOR MEDICAL PRODUCTS

BACKGROUND OF THE INVENTION

Various types of valves incorporating sealing devices are known and widely used in the medical field. For example, mechanical sealing valves are required for various types of catheters, lavage devices, and endoscopy systems developed for a wide range of medical purposes. The valve sealing mechanisms typically preclude the flow of substances (gaseous or fluid) through the medical device in one direction, for example from the patient to the outside environment, while permitting the introduction or flow of desired substances (food, medication, etc.) in the other direction, for example into the patient through the medical device. Enteral feeding devices utilizing a gastrostomy catheter ("feeding tube") are examples of conventional medical devices utilizing a sealing valve to prevent gastric fluids, gases, or particles from unintentionally exiting the patient's body via the catheter. U.S. Pat. Nos. 5,997,503 and 5,997,546, both owned by Applicants' Assignee and incorporated by reference herein, disclose balloon catheters suitable for use as skin-level gastrostomy catheters for enteral feeding. Various other devices and catheters have also been proposed for gastrostomy feeding and are known to those skilled in the art.

Conventional sealing valves include duckbill valves, flap valves, slit seal valves, etc. Silicone rubber duckbill seals having durometer ratings of about 50 Shore and a wall thickness of about 0.040 inches have been employed in sealing gastrostomy catheters. Such sealing valves are typically kept closed via back pressure present on one side of the valve unless and until the seal is opened from the other side of the valve by insertion of a feeding tube or by a pressure differential across the seal.

Over time, conventional sealing valves may degrade or lose some of their flexibility (i.e., their ability to return to an initial sealing position after deflection) due to repeated or extended periods of opening of the valve. Also, in certain bodily environments, such as the acidic environment of the gastrointestinal tract, exposure to bodily fluids or stomach contents may have a corrosive or other negative effect on the sealing valve over time.

Thus, there is a need for an improved medical sealing valve for use in various medical devices, particularly gastrostomy catheter devices.

SUMMARY OF THE INVENTION

Objects and advantages of the invention will be set forth in part in the following description or may be apparent from the description or may be learned through practice of the invention.

It should be noted that any given range presented herein is intended to include any and all lesser included ranges. For example, a range of from 45–90 would also include 50–90, 45–80, 46–89, and the like.

According to the invention, an improved sealing valve assembly is provided for use in a wide array of medical products, including catheters, lavage devices, endoscopy systems, etc. The valve assembly according to the invention is not limited in its particular use and may be used in any medical product wherein it is necessary to permit fluid flow through the product in one direction while preventing backflow of fluids through the product in the opposite direction. For example, the valve assembly is particularly useful in a gastrostomy catheter. Accordingly, it should be appreciated that the present invention also includes medical products or devices incorporating the inventive valve assembly.

The valve assembly includes a valve housing defining a passageway therethrough. A valve member is seated in the valve housing within the passageway. The valve member includes a peripheral portion spaced from the central axis of the valve assembly and two walls extending from the peripheral portion towards the central axis. The walls include ends that contact and seal against each other to preclude flow through the passageway. The valve member may be formed of a material having a durometer of less than about 20 Shore.

In another embodiment, the valve member walls may define a cross-section that tapers in thickness from about 0.005 to 0.010 inches at their respective sealing end to about 0.040 inches at a location spaced from the sealing end. The walls may taper continuously or discontinuously.

In accordance with another aspect of the invention, at least one of the valve member walls may define an overlapping portion extending at an angle with respect to a plane of the remaining portion of the wall. This overlapping portion overlaps and seals against a portion of the other wall. The overlapping portion may be parallel to the other wall.

In accordance with yet another aspect of the invention, the valve member walls may include a first portion including a material having a durometer of about 50 Shore and a second portion having a durometer of less than about 20 Shore. The second portion is disposed at the sealing end of the wall. The first portion is disposed spaced from the sealing end.

The invention will be described in greater detail below with reference to the figures.

DETAILED DESCRIPTION

Embodiments of the invention will now be described in detail with reference to the examples shown in the figures. Each example is provided by way of explaining the invention, and not as a limitation of the invention. Various modifications and variations can be made in the invention without departing from the scope and spirit of the invention. For example, features illustrated or described with respect to one embodiment may be used in another embodiment to yield still a further embodiment.

In the following description, the improved sealing device is described with reference to a gastrostomy catheter for purposes of explaining and illustrating the sealing valve assembly. This is not meant as a limitation of the invention. It should be appreciated that the improved sealing device according to the present invention has wide application in the medical field and can be used in any medical device that incorporates a seal to prevent the flow of substances in one direction while permitting the flow of substances in the opposite direction.

Figure 1:
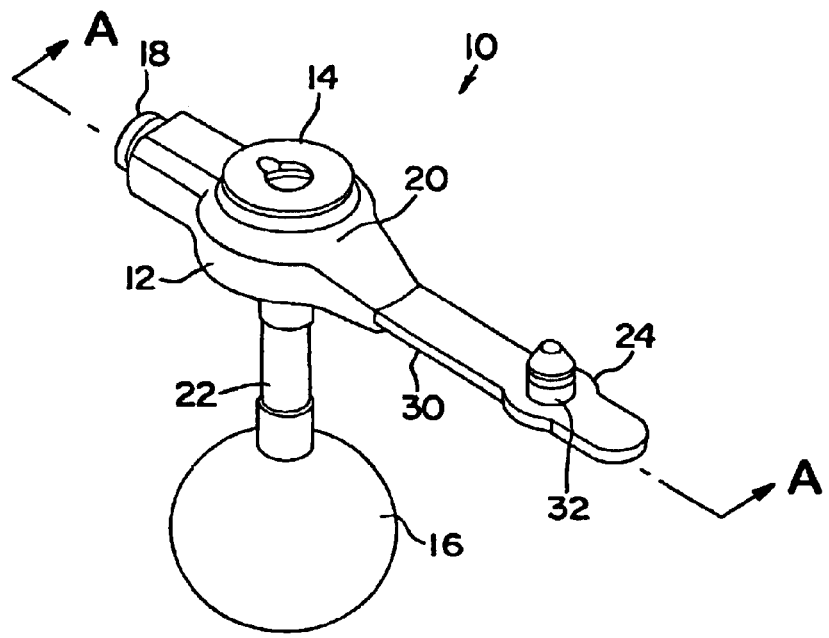
FIG. 1 is a perspective view of a medical product, in particular a gastrostomy catheter, according to the present invention.
Figure 2:
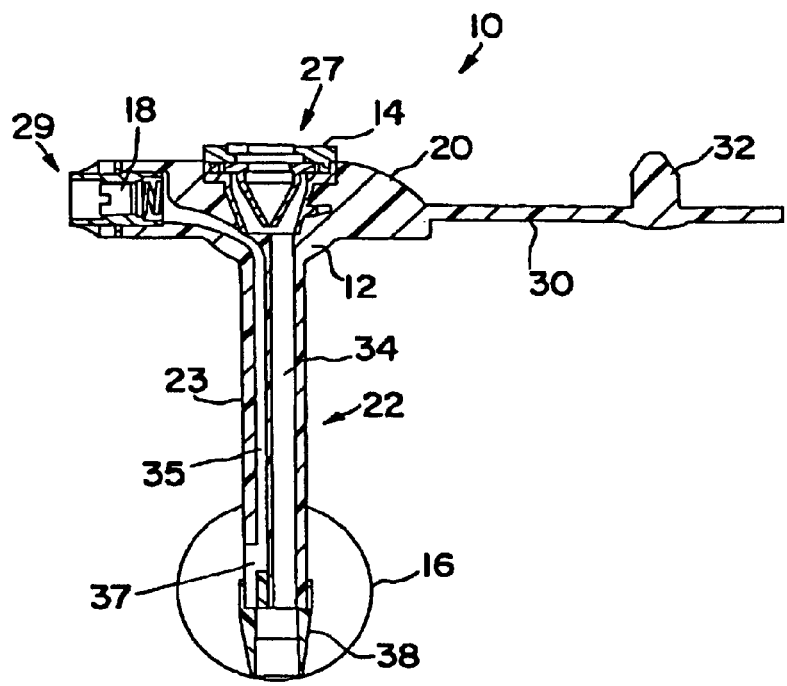
FIG. 2 is a cross-sectional view of the gastrostomy catheter of FIG. 1 taken along line A—A of FIG. 1 particularly illustrating a valve assembly disposed within a catheter body element.

A gastrostomy catheter 10 is shown in FIGS. 1 and 2 as an example of a medical product incorporating the improved valve sealing assembly according to the present invention. The use and operation of such gastrostomy catheters is known to those skilled in the art and need not be described in detail herein. Reference is made to U.S. Pat. Nos. 5,997,546 and 5,997,503 incorporated herein by reference for a detailed explanation of gastrostomy catheters.

As used herein, the term "distal" refers to the direction of the patient and the term "proximal" refers to the direction of the clinician.

Referring briefly to FIGS. 1 and 2, the gastrostomy device 10 includes a catheter body element 12 having a head 20, an elastomeric sleeve forming a balloon 16, and a catheter segment 22. The catheter segment 22 includes a shaft 23 having a dispensing tip 38 attached to its distal end. A first central opening or port 27 in the head 20 incorporates a valve housing assembly 14 that enables the injection of nutrients, enteral feeding solution, medications, etc., into the patient through the head 20 and into a first lumen 34 of the catheter segment 22. The valve housing assembly 14 includes the improved sealing valve according to the invention, as described in greater detail below. A plug 32 may be provided at the end of a lanyard 30 attached to the catheter head 20. The plug 32 can be inserted into the first port 27 when the port is not being used to administer fluids into the patient.

A second port 29 in the head 20 serves as an opening through which fluid such as air or saline solution may be injected into or removed from the balloon 16 through a second lumen 35 having a distal opening 37. An inflation valve assembly 18 is disposed in the second port 29 for permitting the clinician to control inflation and deflation of the balloon 16, as is understood by those skilled in the art.

Figure 3:
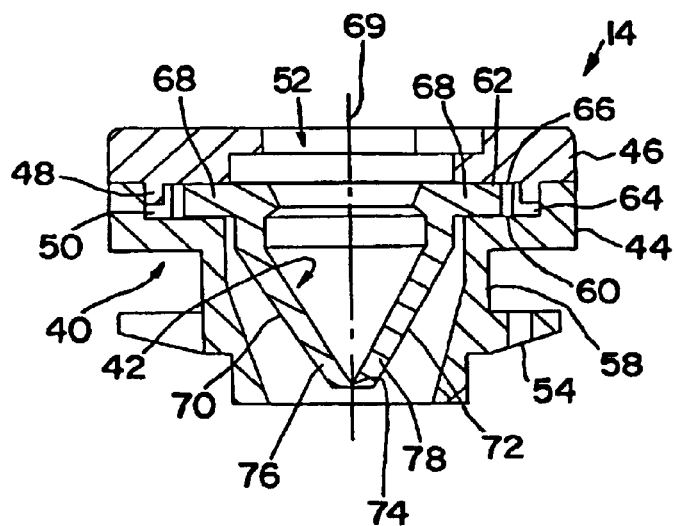
FIG. 3 is an enlarged cross-sectional view of the valve assembly of FIG. 2 taken along line A—A of FIG. 1.
Figure 4:
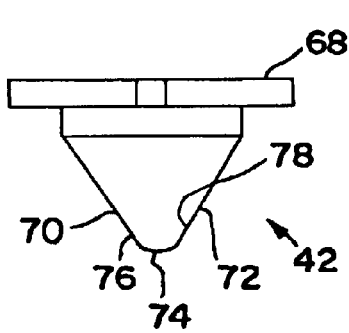
FIG. 4 is a side view of a first embodiment of the valve member of the valve assembly from the perspective taken in FIG. 3.
Figure 5:
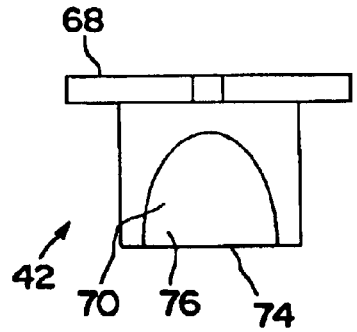
FIG. 5 is a side view of the valve member of FIG. 4 rotated 90 degrees.
Figure 6:
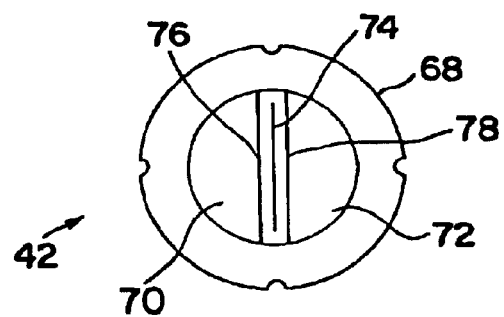
FIG. 6 is a top view of the valve member of FIG. 4.

The valve housing assembly 14 is shown in greater detail in FIG. 3. The valve housing assembly 14 includes a valve housing 40 and the improved sealing valve member 42. The valve housing 40 has an annular member 44 and a relatively flat cap member 46 connected to the annular member 44, for example by a press-fit or an adhesive. The cap member 46 may have a ridge 48 that fits within a groove 50 in the annular member 44 for securing the two parts together. The valve housing 40 includes a flange 54 that extends into a corresponding groove in the catheter body element 12 to seat and secure the valve housing therein. The flange 54 extends radially from a lower tubular portion 58 of the valve housing 40. The tubular portion 58 may have inner walls that angle towards a centerline axis 69 of the valve housing assembly 14. The walls of the tubular portion 58 parallel to the plane of FIG. 3 may be parallel to the axis 69.

A passage 52 is defined through both portions of the valve housing assembly 14. The passage 52 is in fluid communication with the feeding lumen 34 through the valve member 42 for introducing nutrients, feeding solutions, medication, etc., into the patient's stomach, intestine, or other body cavity. The valve member 42 is disposed within the passage 52 for selectively blocking the fluid path through feeding lumen 34.

The valve member 42 incorporates novel features of the present invention and various embodiments of the valve member 42 are partially shown in FIGS. 3–10. Referring to FIG. 3, the valve member 42 includes a proximal flange portion 68 disposed between facing surfaces 64, 66 of the annular member 44 and the cap member 46. Small circular ridges 60,62 on the facing surfaces 64,66 engage the flange portion 68 and help to seat and hold the valve member 42 in place. The valve member 42 includes two walls 70, 72 on opposite sides of the central axis 69 that extend from the peripheral portion 68 and are angled towards the central axis 69. The walls 70,72 meet at a single seal interface 74 defined by ends 76,78 of the walls. Parts 68, 70, and 72 form what is known in the art as a duckbill valve. As explained in greater detail below, to achieve satisfactory sealing, the thickness and profile of the walls 70,72 may be designed in various ways according to the present invention depending on the durometer of the material used for the valve member 42.

Figure 7:
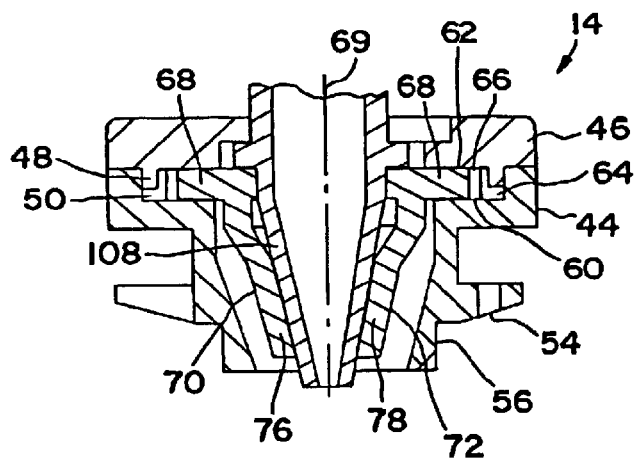
FIG. 7 is a cross-sectional view of the assembly of FIG. 3 with the end of a feeding tube inserted therein.

The seal interface 74 is biased to a closed position and maintained in the closed position by body cavity pressure unless forced open by an object inserted into the valve member 42 through the cap member 46 or by a significant pressure differential between the patient cavity and the external environment. An object useful to open the valve member 42 could be a feeding tube, a feeding tube adapter, or a pressure relief tube. As an example, FIG. 7 shows the valve housing assembly 14 of FIG. 3 with the end of a feeding tube 108 inserted therein. Note that the tube end 108 pushes open the walls 70,72 of valve member to allow communication with the patient's body cavity through the valve housing 14 and feeding lumen 34.

The various components of medical device 10 are preferably formed from bio-compatible materials such as medical grade silicone. More particularly, the valve member 42 may be made of a liquid injection molding silicone elastomer such as MED-4810 (10 Shore Durometer) or MED-4820 (20 Shore Durometer), available from NuSil Technology of Carpintera, Calif. The valve member is molded, and the sealing interface 74 is created by slitting or cutting apart the respective walls after molding.

As mentioned, the thickness and profile of the walls 70, 72 will depend on the durometer of the material used to form the valve member 42. For example, for a wall thickness of about 0.040 inches, the durometer of the valve member may be about 20 or less, and may be in the range of from about 8 to about 15, and more particularly about 10. Applicants have discovered that use of a substantially lower durometer material than had been used previously in the art for the valve member unexpectedly provides an improved seal and greater seal flexibility without sacrificing the structural integrity of the valve member.

However, if the durometer of the valve member 42 is higher, such as up to about 50 as has been used previously, the wall cross sections of the valve member can be altered to provide improved seal flexibility. For example, alternate embodiments of the valve member 42 are shown in FIGS. 8–10.

Figure 8:
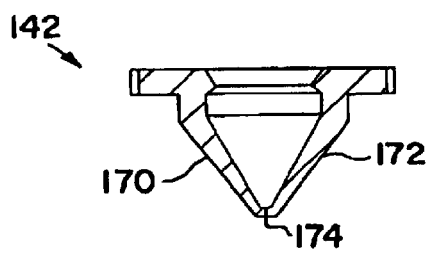
FIG. 8 is a cross-sectional view of an alternate embodiment of a valve member.
Figure 9:
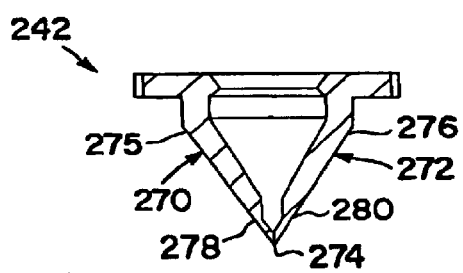
FIG. 9 is a cross-sectional view of a second alternate embodiment of a valve member.

The valve members in FIGS. 8 and 9 have walls with a varying cross-section. The valve member 142 in FIG. 8 includes two walls 170,172 that are continuously tapered, narrowing toward the sealing interface 174. The walls may taper up to about 15% of their upper wall thickness. For example, the walls 170, 172 may taper from 0.040 inches to approximately 0.005 to 0.010 inches at the seal interface. The valve member 242 in FIG. 9 includes two walls 270, 272 having a constant cross-sectional thickness along their upper portions 274, 276 of about 0.040 inches and reduced thickness edge portions 278, 280 having a thickness of about 0.005 to 0.010 inches. The valve member 342 in FIG. 10 has walls 370, 372 which may have a thickness throughout of about 0.040 inches. The wall 372 has an edge portion angled with respect to the remaining portion of the wall 372. The angled portion 380 is parallel to and overlaps a portion 378 of the wall 370. The overlapping edge portions 378, 380 may have a thickness and length of about 0.040 inches.

Figure 10:
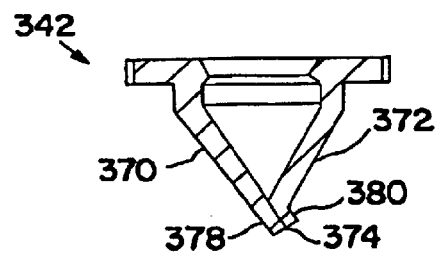
FIG. 10 is a cross-sectional view of a third alternate embodiment of a valve member.

Each of the valve members of FIGS. 8–10 may be molded of relatively high durometer materials, with the modified wall structure providing improved sealing and wall flexibility.

As another option, a valve member 42 having a shape as shown in FIGS. 3–7 could be molded having a varying durometer that decreases in the direction of the seal interface. In such a valve member, the peripheral portion 68 and the upper portion of a wall or the walls 70,72 may be made from a material of relatively higher durometer (for example in the range of about 50 Shore), and the remaining portion may be made of a lower or a gradiently decreasing durometer material (for example, decreasing to the range of about 20 Shore or less, more particularly about 8 to about 15 Shore, and even more particularly to about 10 Shore). The softer tip of the walls 70,72 would thus provide improved sealing while the harder upper portion would maintain the shape of the valve member.

Thus, applicants have disclosed above numerous designs and/or material selections that provide for improved sealing across the seal interface of a valve member as well as improved flexibility of the valve member. Such improved sealing flexibility may provide a longer lifespan to medical devices such as gastrostomy catheters and to the valve members and related valve assemblies used therein. Such improved sealing may also provide a more reliable product in terms of reducing or eliminating undesired leakage.

It should be appreciated by those skilled in the art that various modifications and variations can be made in the present invention without departing from the scope and spirit of the invention. It is intended that the invention include such modifications and variations as come within the full scope of the appended claims and any equivalents thereof.

What is claimed is:

1. A valve assembly for use in a medical product having a fluid path, the valve assembly configured to selectively pass fluids in one direction along the fluid path and to prevent backflow in the opposite direction along the fluid path, the valve assembly comprising:

a valve housing defining an opening having a central axis, the opening extending through the valve housing such that the opening forms part of the fluid path through the medical product;

a valve member disposed within the opening, the valve member having a single seal interface defined by at least two opposing flexible walls biased towards each other to a sealing position, the valve member having a peripheral portion with the opposing flexible walls extending from the peripheral portion toward the central axis, the opposing flexible walls including ends that contact each other along the single seal interface; and the valve member formed at least in part by a material having a durometer of less than about 20 Shore A.

2. The valve assembly as in claim 1, wherein the opposing walls of the valve member each have a generally uniform thickness of about 0.040 inches.

3. The valve assembly as in claim 1, wherein the valve member material has a durometer of about 8 to 15 Shore A.

4. The valve assembly as in claim 1, wherein the valve member peripheral portion and walls form a duckbill valve.

5. A medical product defining a fluid path, the medical product comprising a valve assembly disposed in the path, the valve assembly comprising:

a valve housing defining an opening having a central axis, the opening extending through the valve housing such that the opening forms part of the fluid path through the medical product;

a valve member disposed within the opening, the valve member having a single seal interface defined by at least two opposing flexible walls biased towards each other to a sealing position, the valve member having a peripheral portion with the opposing flexible walls extending from the peripheral portion toward the central axis, the opposing flexible walls including ends that contact each other along the single seal interface; and the valve member formed at least in part by a material having a durometer of less than about 20 Shore A.

6. The medical product as in claim 5, wherein the medical product is a gastrostomy catheter, the fluid path defined between a patient=s body cavity and an exterior of the body.

7. A valve assembly for use in a medical product having a fluid path, the valve assembly configured to selectively pass fluids in one direction along the fluid path and to prevent backflow in the opposite direction along the fluid path, the valve assembly comprising:

a valve housing defining an opening having a central axis, the opening extending through the valve housing such that the opening forms part of the fluid path through the medical product;

a valve member disposed within the opening, the valve member having a single seal interface defined by at least two opposing flexible walls biased towards each other to a sealing position, the valve member having a peripheral portion with the opposing flexible walls extending from the peripheral portion toward the central axis, the opposing flexible walls including ends that contact each other along the single seal interface; and at least one of the flexible opposing walls defining a first portion including a material having a durometer of about 50 Shore A and a second portion having a durometer of less than about 20 Shore A, the second portion being disposed at the respective end of the at least one wall, and the first portion being disposed spaced from the respective end.

8. The valve assembly as in claim 7, wherein the at least one wall has a thickness of about 0.040 inches.

9. The valve assembly as in claim 7, wherein the second portion of the at least one wall includes a material having a durometer of about 10 Shore A.

10. A medical product defining a fluid path, the medical product comprising a valve assembly disposed in the path, the valve assembly comprising:

a valve housing defining an opening having a central axis, the opening extending through the valve housing such that the opening forms part of the fluid path through the medical product;

a valve member disposed within the opening, the valve member having a single seal interface defined by at least two opposing flexible walls biased towards each other to a sealing position, the valve member having a peripheral a portion with the opposing flexible walls extending from the peripheral portion toward the central axis, the opposing flexible walls including ends that contact each other along the single seal interface; and at least one of the flexible opposing walls defining a first portion including a material having a durometer of about 50 Shore A and a second portion having a durometer of less than about 20 Shore A, the second portion being disposed at the respective end of the at least one wall, and the first portion being disposed spaced from the respective end.

11. The medical product as in claim 10, wherein the medical product is a gastrostomy catheter, the fluid path defined between a patient=s body cavity and an exterior of the body.

12. The medical product as in claim 5, wherein the valve member has a durometer of about 8 to less than 10 Shore A.

* * * * *

UNITED STATES PATENT AND TRADEMARK OFFICE
CERTIFICATE OF CORRECTION

PATENT NO. : 6,908,449 B2
DATED : June 21, 2005
INVENTOR(S) : Allan F. Willis and Alan Conlin It is certified that error appears in the above-identified patent and that said Letters Patent is hereby corrected as shown below:

Column 6,
Line 4, "about 20 Shore A" should read -- 10 Shore A --.
Line 9, "15 Shore A" should read -- less than 10 Shore A --.
Line 28, "about 20 Shore A" should read -- 10 Shore A --.

Signed and Sealed this

Eighteenth Day of October, 2005

JON W. DUDAS
*Director of the United States Patent and Trademark Office*